United States Patent
Dockal et al.

(10) Patent No.: US 11,160,850 B2
(45) Date of Patent: Nov. 2, 2021

(54) COMPOSITIONS OF HUMAN PROTHROMBIN AND ACTIVATED FACTOR X FOR IMPROVING HEMOSTASIS IN THE TREATMENT OF BLEEDING DISORDERS

(71) Applicants: Baxalta Incorporated, Bannockburn, IL (US); Baxalta GmbH, Zug (CH)

(72) Inventors: Michael Dockal, Vienna (AT); Sabine Knappe, Vienna (AT); Susanne Till, Vienna (AT); Peter Leopold Turecek, Klosterneuburg (AT); Friedrich Scheiflinger, Vienna (AT)

(73) Assignee: Takeda Pharmaceutical Company Limited, Osaka (JP)

( * ) Notice: Subject to any disclaimer, the term of this patent is extended or adjusted under 35 U.S.C. 154(b) by 271 days.

(21) Appl. No.: 16/231,195

(22) Filed: Dec. 21, 2018

(65) Prior Publication Data

US 2019/0231855 A1     Aug. 1, 2019

Related U.S. Application Data

(62) Division of application No. 14/658,006, filed on Mar. 13, 2015, now abandoned.

(60) Provisional application No. 61/953,496, filed on Mar. 14, 2014.

(51) Int. Cl.
    *A61K 38/48*         (2006.01)
    *A61K 38/54*         (2006.01)

(52) U.S. Cl.
    CPC ...... *A61K 38/4833* (2013.01); *A61K 38/4846* (2013.01); *A61K 38/54* (2013.01); *C12Y 304/21005* (2013.01); *C12Y 304/21006* (2013.01)

(58) Field of Classification Search
    CPC ................ A61K 38/4833; A61K 38/54; A61K 38/4846; A61K 2300/00; C12Y 304/21005; C12Y 304/21006; A61P 7/04; A61P 43/00
See application file for complete search history.

(56) References Cited

U.S. PATENT DOCUMENTS

| | | |
|---|---|---|
| 4,287,180 A | 9/1981 | Thomas |
| 5,866,122 A | 2/1999 | Turecek et al. |
| 9,956,272 B2 | 5/2018 | Lloyd et al. |
| 2015/0258182 A1 | 9/2015 | Dockal et al. |

FOREIGN PATENT DOCUMENTS

| | | |
|---|---|---|
| CN | 102905732 A | 1/2013 |
| WO | WO 2015/138847 A1 | 9/2015 |

OTHER PUBLICATIONS

Frachini et al., Past, present and future of hemophilia: a narrative review. Orphanet J Rare Dis. May 2, 2012;7:24. doi: 10.1186/1750-1172-7-24.

Himmelspach et al., A fully recombinant partial prothrombin complex effectively bypasses fVIII in vitro and in vivo. Thromb Haemost. Dec. 2002;88(6):1003-11.

Mitterlechner et al., Prothrombin complex concentrate and recombinant prothrombin alone or in combination with recombinant factor X and FVIIa in dilutional coagulopathy: a porcine model. J Thromb Haemost. Apr. 2011;9(4):729-37. doi: 10.1111/j.1538-7836.2011.04211.x.

Nakatomi et al., Combining FVIIa and FX into a mixture which imparts a unique thrombin generation potential to hemophilic plasma: an in vitro assessment of FVIIa/FX mixture as an alternative bypassing agent. Thromb Res. May 2010;125(5):457-63. doi: 10.1016/j.thromres.2009.12.010. Epub Jan. 18, 2010.

Turecek et al., Factor Xa and prothrombin: mechanism of action of FEIBA. Vox Sang. 1999;77 Suppl 1:72-9.

Turecek et al., FEIBA: mode of action. Haemophilia. Sep. 2004;10 Suppl 2:3-9.

Varadi et al., PP-TH-611—New insights into the role of hermostatic components (FEIBA). J Thromb Haemost. Jul. 2009;10(S2):1137-1138.

[No Author Listed], Neue Arzneimittel Xarelto. Jul. 10, 2013; 4 pages.

[No Author Listed], Neue Arzneimittel. Pradaxa. Nov. 18, 2011; 4 pages.

Awad et al., Activated prothrombin complex concentrates for the reversal of anticoagulant-associated coagulopathy. P T. Nov. 2013;38(11):696-701.

Hubbard A.R., International biological standards for coagulation factors and inhibitors. Semin Thromb Hemost. Apr. 2007;33(3):283-9. doi: 10.1055/s-2007-971815.

Jackson, Factor X. In Human Protein Data. Ed. Haeberli.1998; 1st Edition. Part A. Five pages.

Jackson, Prothrombin (F II). In Human Protein Data. Ed. Haeberli. 1998; 1st Edition. Part B. Five pages.

Lazo-Langner et al., Clinical review: Clinical management of new oral anticoagulants: a structured review with emphasis on the reversal of bleeding complications. Crit Care. Jun. 17, 2013;17(3):230. doi: 10.1186/cc12592.

Scipio et al., Activation of human factor X (Stuart factor) by a protease from Russell's viper venom. Biochemistry. Nov. 29, 1977;16(24):5253-60. doi: 10.1021/bi00643a015.

*Primary Examiner* — Lynn Y Fan

(74) *Attorney, Agent, or Firm* — Wolf, Greenfield & Sacks, P.C.

(57) ABSTRACT

Disclosed herein are compositions and methods for improving hemostasis in the treatment of bleeding disorders and reversal of anticoagulant activity. Effective ratios of prothrombin (FII) and activated factor X (FXa) for the treatment of bleeding disorders that are as efficacious as FEIBA®, but require a lower concentration of FII are described herein.

12 Claims, 4 Drawing Sheets

COMPOSITIONS OF HUMAN PROTHROMBIN AND ACTIVATED FACTOR X FOR IMPROVING HEMOSTASIS IN THE TREATMENT OF BLEEDING DISORDERS

CROSS REFERENCE TO RELATED APPLICATIONS

This application is a Division of U.S. application Ser. No. 14/658,006, filed Mar. 13, 2015, entitled "COMPOSITIONS OF HUMAN PROTHROMBIN AND ACTIVATED FACTOR X FOR IMPROVING HEMOSTASIS IN THE TREATMENT OF BLEEDING DISORDERS", which claims the benefit of U.S. Provisional Patent Application No. 61/953,496, filed Mar. 14, 2014, the entire contents of each of which are hereby incorporated by reference.

FIELD

Disclosed herein are compositions and methods for improving hemostasis in the treatment of bleeding disorders and reversal of anticoagulant activity.

BACKGROUND

The coagulation cascade by which the human body produces blood clots is the body's primary mechanism to stop bleeding. Blood clots are produced by platelets sticking together in a fibrin matrix to form a plug at an injured blood vessel site. The body's inability to form blood clots can lead to excessive bleeding which can be very dangerous. Blood which cannot clot properly in an individual is often the sign of a bleeding disorder.

The inability to form blood clots may be due to a deficiency or lack of clotting factors in the coagulation cascade. For instance, hemophilia A, the most common type of hemophilia, is a largely inherited bleeding disorder in which there is a Factor VIII (FVIII) deficiency. For a person with hemophilia A that gets injured, bleeding is not stopped easily and requires a longer time to be arrested. The development of antibodies, also called inhibitors, against FVIII in response to FVIII replacement therapy is an additional challenge for treatment of hemophilia A.

A less common type of hemophilia, hemophilia B, is also a largely inherited bleeding disorder that results in a Factor IX (FIX) deficiency and is also known as "Christmas disease." The development of antibodies, also called inhibitors, against FIX in response to FIX replacement therapy is an additional challenge for treatment of hemophilia B.

Another bleeding disorder, von Willebrand disease, also an inherited genetic disease, is caused by a deficiency or defect in the von Willebrand factor (vWF), a blood clotting protein. The vWF is critical in the initial stages of blood clotting as it interacts with the platelets to form a plug at the site of injury.

Treatment of bleeding disorders usually involves replacing the blood clotting factor which is either lacking or deficient. The factors can either be purified from donated human plasma (plasma-derived factors), or made recombinantly (recombinant factors).

Antibodies, also called inhibitors, can develop when an individual with a bleeding disorder is treated with FVIII replacement therapy and the body recognizes the therapy as a threat instead of treatment. In response to the perceived threat the immune system makes antibodies, also called inhibitors, which attack FVIII. This can be very dangerous as the inhibitors can prevent or inhibit FVIII from controlling bleeding. Therefore, in the case of development of inhibitors against the administered clotting factor, bypass therapies have to be applied. Treatment of hemophilia A is complicated by development of FVIII neutralizing antibodies, occurring in about 30% of patients with severe hemophilia A. Similar inhibitory or neutralizing antibody formation can occur in patients treated with FIX or vWF replacement therapy. Currently there are two standard treatment options for hemophilia patients who have developed inhibitors against FVIII or FIX: monotherapy with FEIBA® (Baxter Healthcare Corporation, Deerfield, Ill.) or recombinant FVIIa. There are other options such as using prothrombin complexes or even plasma exchange, but they have more side effects and are not as efficacious. FEIBA® (factor eight inhibitor bypassing activity) has been used for over thirty years in the treatment of patients with hemophilia. It is an integral part of bypass therapy in hemophiliacs with inhibitors, controls bleeding in 93% of episodes, and has a high safety profile. Some patients are refractory or non-responsive to monotherapy with FEIBA® or recombinant FVIIa thus, there is a need for improvement of inhibitor therapy in the art. The inventors have identified effective ratios of human prothrombin (FII) and activated factor X (FXa) for the treatment of bleeding disorders that are as efficacious as FEIBA®, but require a lower amount of FII. FII and FXa can either be recombinant or plasma-derived.

SUMMARY

The present compositions and methods are directed towards improving hemostasis in the treatment of bleeding disorders and aiding in the reversal of anticoagulant activity.

Effective ratios of prothrombin (FII) and activated factor X (FXa) are herein described to aid in the treatment of bleeding disorders and the reversal of anticoagulant activity. FII and FXa can either be recombinant or plasma-derived.

Certain embodiments include a composition for treating a bleeding disorder comprising FII and FXa wherein the molar ratio of FXa to FII is more than 1:20,000.

In other embodiments, a composition for treating a bleeding disorder comprises about 0.44 mg/kg of FII and about 826 ng/kg of FXa. Alternatively, the composition can comprise about 0.2 mg/kg to about 1 mg/kg of FII and about 560 ng/kg to about 1100 ng/kg of FXa. Alternatively, the composition can comprise about 4.4 mg/kg of FII and about 275 ng/kg of FXa. Alternatively, the composition can comprise about 1.2 mg/kg to about 5 mg/kg of FII and about 200 ng/kg to about 540 ng/kg of FXa.

In yet other embodiments, a bleeding disorder can include hemophilia A, hemophilia B, von Willebrand disease, congenital hemophilia A with inhibitors or acquired hemophilia A with inhibitory auto antibodies to FVIII, congenital hemophilia B with inhibitors or acquired hemophilia B with inhibitory auto antibodies to FIX, blood loss from trauma, Factor VII (FVII) deficiency, Factor V (FV) deficiency, Factor X (FX) deficiency, Factor XI (FXI) deficiency, Factor XIII (FXIII) deficiency, fibrinogen deficiency, prothrombin deficiency, dilutional coagulopathy, thrombocytopenia, blood loss from high-risk surgeries, intracerebral hemorrhage, von Willebrand disease with inhibitors to von Willebrand factor, or combinations thereof.

Other embodiments include a pharmaceutical composition for treating a bleeding disorder comprising FII and FXa wherein the molar ratio of FXa to FII is more than 1:20,000 and at least one excipient. FII and FXa can either be plasma derived or recombinant In certain embodiments, a pharmaceutical composition can include about 0.44 mg/kg of FII and about 826 ng/kg of FXa and at least one excipient. Alternatively, the pharmaceutical composition can comprise about 0.2 mg/kg to about 1 mg/kg of FII and about 560 ng/kg to about 1100 ng/kg of FXa and at least one excipient. Alternatively, the pharmaceutical composition can comprise about 4.4 mg/kg of FII and about 275 ng/kg of FXa and at least one excipient. Alternatively, the pharmaceutical composition can comprise about 1.2 mg/kg to about 5 mg/kg of FII and about 200 ng/kg to about 540 ng/kg of FXa and at least one excipient.

In other embodiments, a method of treating a bleeding disorder comprises administering a composition comprising FII and FXa wherein the molar ratio of FXa to FII is more than 1:20,000 is described. FII and FXa can either be recombinant or plasma-derived.

Yet further embodiments include a composition for aiding in the reversal of anticoagulant activity comprising FII and FXa wherein the molar ratio of FXa to FII is more than 1:20,000. FII and FXa can either be recombinant or plasma-derived.

BRIEF DESCRIPTION OF THE DRAWINGS

FIG. 3A is a schematic overview of the experimental procedure. FIG. 3B is a diagram illustrating relative blood loss following a nail cut which was monitored for 30 minutes before and after intravenous administration of FII and/or FXa, FEIBA® (positive control), or buffer (negative control). The median for each group is indicated as a black line.

DETAILED DESCRIPTION

Figure 1:
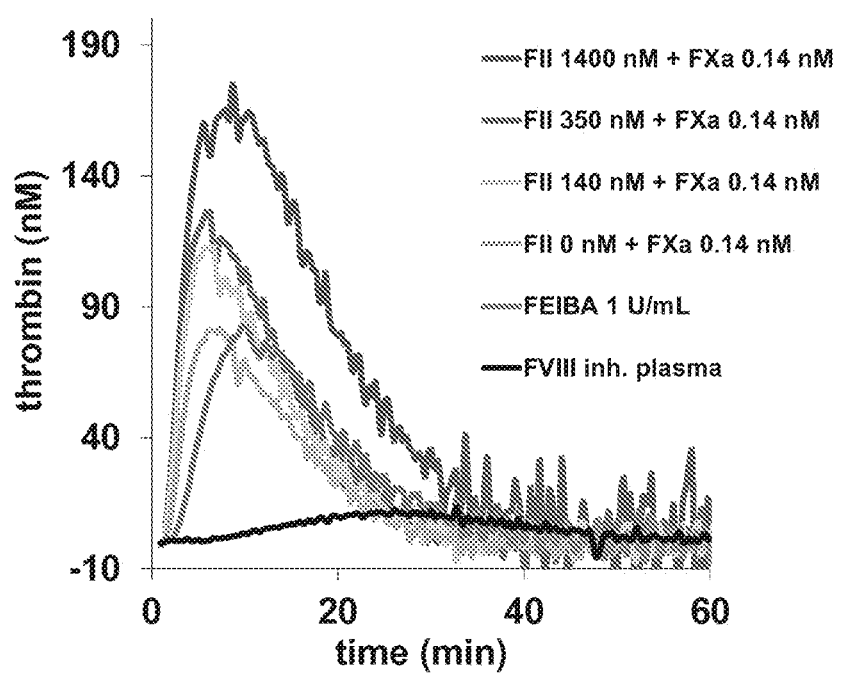
FIG. 1 is a diagram illustrating representative thrombin generation profiles of different combinations of human pro-thrombin (FII) and activated factor X (FXa) in FVIII-inhibited human plasma.

Effective ratios of human prothrombin (FII) and activated factor X (FXa) are herein described to aid in the treatment of bleeding disorders and the reversal of anticoagulant activity.

Disclosed herein are compositions for treating a bleeding disorder comprising FII and FXa wherein the molar ratio of FXa to FII is more than 1:20,000. FII and FXa can either be plasma derived or recombinant.

The production of recombinant proteins such as FII and FXa is well known in the art. For example, EP 1460131 describes a process for producing recombinant human blood clotting factors in human cell lines. Further, WO 2005/038019 describes producing high yields of coagulation factors recombinantly. The process of isolating coagulation factors from plasma products is also well known in the art. For example, U.S. Pat. No. 4,883,598 describes the process for isolating coagulation factors from blood plasma or plasma products using liquid chromatography.

FEIBA® is a plasma-derived activated prothrombin complex concentrate used to treat bleeding episodes in hemophilic patients with inhibitors. FII and FXa have been identified as the most critical components that mediate the hemostatic effect of FEIBA®. The molar ratio of FXa and FII in FEIBA® ranges from 1:20,000-40,000, i.e. 1 U/mL of FEIBA® results in plasma concentrations of 0.035-0.07 nM FXa and 1400 nM FII. The molar ratio ranges of FXa to FII in FEIBA® results in a high prothrombin requirement which is challenging to produce recombinantly. FII and FX are complex proteins with multiple structural domains and post-translational modifications. Both can be produced recombinantly in mammalian cell lines, e.g. CHO. Factor X needs to be further activated to FXa for co-formulation with FII in the compositions of the present embodiments.

Hemophiliac patients "with inhibitors" can mean hemophiliac patients with antibodies, with neutralizing antibodies, with inhibitory antibodies or the like. The inhibitors can develop when an individual with a bleeding disorder is treated with a replacement therapy and the body recognizes the therapy as a threat instead of treatment.

In the past, recombinant partial prothrombinase has been developed based on the FXa/FII ratio that is present in FEIBA® to explore the efficacy of this combination of coagulation factors. However, in this approach the expression and production of high amounts of recombinant FII was the limiting factor. Studies were performed to identify effective ratios of human FII and FXa that are as active and efficacious as FEIBA®, but require a lower amount of FII. Further, exploratory expression studies by using state-of-the-art expression platforms and clone screening technologies demonstrated technical feasibility of recombinant factor X and prothrombin generation. State-of-the-art expression system in CHO cells provided high yields at high protein quality and potency for both factors. Combination of recombinant FXa and prothrombin may be used as an option for hemophilia inhibitor therapy. An additional benefit of the compositions of the present embodiments may be decreased risk of thrombosis, as the FII concentration is lower this may lead to fewer spontaneous clotting events, especially when used in non-hemophilic patients for anticoagulant reversal.

Surprisingly, it was found that ratios of FII to FXa very different from those found in FEIBA® were as effective at controlling bleeding. In certain embodiments, a composition for treating bleeding disorders comprises FII and FXa wherein the molar ratio of FXa to FII is more than about 1:20,000, more than about 1:19,000, more than about 1:18,000, more than about 1:17,000, more than about 1:16,000, more than about 1:15,000, more than about 1:14,000, more than about 1:13,000, more than about 1:12,000, more than about 1:11,000, more than about 1:10,000, more than about 1:9,000, more than about 1:8,000, more than about 1:7,000, more than about 1:6,000, more than about 1:5,000, more than about 1:4,000, more than about 1:3,000, more than about 1:2,000, more than about 1:1,000, more than about 1:950, more than about 1:900, more than about 1:850, more than about 1:800, more than about 1:750, more than about 1:700, more than about 1:650, more than about 1:600, more than about 1:550, more than about 1:500, more than about 1:450, more than about 1:400, more than about 1:350, more than about 1:300, more than about 1:250, more than about 1:200, more than about 1:150, more than about 1:100, more than about 1:95, more than about 1:90, more than about 1:85, more than about 1:80, more than about 1:75, more than about 1:70, more than about 1:65, more than about 1:60, more than about 1:55, more than about 1:50, more than about 1:45, more than about 1:40, more than about 1:35, more than about 1:30, more than about 1:25, more than about 1:20, more than about 1:15, more than about 1:10, or more than about 1:5.

In other embodiments, a composition for treating bleeding disorders comprises FII and FXa wherein the molar ratio of FXa to FII is about 1:19,999, about 1:19,500, about 1:18,500, about 1:17,500, about 1:16,500, about 1:15,500, about 1:14,500, about 1:13,500, about 1:12,500, about 1:11,500, about 1:10,500, about 1:9,500, about 1:8,500, about 1:7,500, about 1:6,500, about 1:5,500, about 1:4,500, about 1:3,500, about 1:2,500, about 1:1,500, about 1:950, about 1:900, about 1:850, about 1:800, about 1:750, about 1:700, about 1:650, about 1:600, about 1:550, about 1:500, about 1:450, about 1:400, about 1:350, about 1:300, about 1:250, about 1:200, about 1:150, about 1:100, about 1:95, about 1:90, about 1:85, about 1:80, about 1:75, about 1:70, about 1:65, about 1:60, about 1:55, about 1:50, about 1:45, about 1:40, about 1:35, about 1:30, about 1:25, about 1:20, about 1:15, about 1:10, or about 1:5.

In other embodiments, a composition for treating bleeding disorders comprises about 0.1 mg/kg of FII and about 800 ng/kg of FXa, about 0.15 mg/kg of FII and about 700 ng/kg of FXa, about 0.2 mg/kg of FII and about 600 ng/kg of FXa, about 0.25 mg/kg of FII and about 500 ng/kg of FXa, about 0.3 mg/kg of FII and about 400 ng/kg of FXa, about 0.35 mg/kg of FII and about 300 ng/kg of FXa, about 0.4 mg/kg of FII and about 200 ng/kg of FXa, about 0.45 mg/kg of FII and about 200 ng/kg of FXa, or about 0.5 mg/kg of FII and about 100 ng/kg of FXa. In yet other embodiments, a composition for treating bleeding disorders comprises about 0.44 mg/kg of FII and about 826 ng/kg of FXa. In other embodiments, a composition for treating bleeding disorders comprises about 4.4 mg/kg of FII and about 275 ng/kg of FXa.

In certain embodiments, a composition for treating bleeding disorders comprises about 0.1 mg/kg to about 0.5 mg/kg of FII and about 600 ng/kg to about 1100 ng/kg of FXa, about 0.5 mg/kg to about 1 mg/kg of FII and about 500 ng/kg to about 1000 ng/kg of FXa, about 1 mg/kg to about 1.5 mg/kg of FII and about 450 ng/kg to about 950 ng/kg of FXa, about 2.0 mg/kg to about 2.5 mg/kg of FII and about 400 ng/kg to about 900 ng/kg of FXa, about 2.5 mg/kg to about 3.0 mg/kg of FII and about 350 ng/kg to about 850 ng/kg of FXa, about 3.5 mg/kg to about 4.5 mg/kg of FII and about 300 ng/kg to about 600 ng/kg of FXa, or about 4.5 mg/kg to about 5.5 mg/kg of FII and about 200 ng/kg to about 600 ng/kg of FXa. In other embodiments, a composition for treating bleeding disorders comprises about 0.2 mg/kg to about 1 mg/kg of FII and about 560 ng/kg to about 1100 ng/kg of FXa. In yet other embodiments, a composition for treating bleeding disorders comprises about 1.2 mg/kg to about 5 mg/kg of FII and about 200 ng/kg to about 540 ng/kg of FXa.

In some embodiments, the FXa is approximately 90% FXaα and 10% FXaβ forms. Alternatively the FXa can be approximately 100% FXaα and 0% FXaβ forms, approximately 80% FXaα and 20% FXaβ forms, approximately 70% FXaα and 30% FXaβ forms, approximately 60% FXaα and 40% FXaβ forms, approximately 50% FXaα and 50% FXaβ forms, approximately 40% FXaα and 60% FXaβ forms, approximately 30% FXaα and 70% FXaβ forms, approximately 20% FXaα and 80% FXaβ forms, approximately 10% FXaα and 90% FXaβ forms, or approximately 0% FXaα and 100% FXaβ forms.

Bleeding disorders include, but are not limited to, hemophilia A, hemophilia B, von Willebrand disease, congenital hemophilia A with inhibitors or acquired hemophilia A with inhibitory auto antibodies to FVIII, congenital hemophilia B with inhibitors or acquired hemophilia B with inhibitory auto antibodies to FIX, blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease with inhibitors to von Willebrand factor, or combinations thereof.

Anticoagulants are used to treat and prevent blood clots. Individuals who are at risk at developing a blood clot, or to prevent an existing blood clot from growing, are given an anticoagulant. Those at risk for developing a blood clot include those with atrial fibrillation, a mechanical heart valve, endocarditis, mitral stenosis, certain blood disorders, and those who have had hip replacement surgery or knee replacement surgery. Sometimes reversal of anticoagulants is necessary for example, in situations where there is a high risk of bleeding. The pharmacological effect of some anticoagulants, for example warfarin, can be readily reversed by the administration of vitamin K. Some more recently introduced anticoagulants such as apixaban, betrixaban, and rivaroxaban cannot be readily reversed by the administration of vitamin K. Currently there is no antidote for unwanted bleeding caused by these anticoagulants which can be quite dangerous. Thus, an additional benefit of the compositions disclosed herein is when used in non-hemophilic patients for anticoagulant reversal, there are fewer spontaneous clotting events.

Routes of administration for the disclosed compositions include, but are not limited to, parenteral injection, intravenous injection, subcutaneous injection, and intramuscular injection.

Dosing can be single dosage or cumulative (serial dosing), and can be readily determined by one skilled in the art. For instance, treatment of congenital hemophilia may comprise administration of an effective dose of a composition disclosed herein for an entire lifetime. As a non-limiting example, an effective dose of a composition disclosed herein can be administered once to an individual, e.g., as a single injection. Alternatively, treatment of a bleeding disorder may comprise multiple administrations of an effective dose of a composition disclosed herein carried out over a range of time periods, such as, e.g., daily, once every few days, or weekly. As a non-limiting example, a composition disclosed herein can be administered twice or three times weekly to an individual. The timing of administration can vary from individual to individual, depending upon such factors as the severity of an individual's symptoms. For example, an effective dose of a composition disclosed herein can be administered to an individual once a day, or every two to three days, for an indefinite period of time. A person of ordinary skill in the art will recognize that the condition of the individual can be monitored throughout the course of treatment and that the effective amount of a composition disclosed herein that is administered can be adjusted accordingly. The clinical efficacy can be described by controlling bleeding. Administration can be on demand, prophylactic, pre-operative or peri-operative.

Certain embodiments include a pharmaceutical composition for treating bleeding disorders comprising plasma-derived FII and FXa wherein the molar ratio of FXa to FII is more than 1:20,000 and at least one excipient. Excipients include, but are not limited to, water, NaCl or other salts for isotonicity, 5% dextrose in water, buffered solutions with a pH of 2-8, trehalose, mannitol, or sorbitol as stabilizers, buffers such as phosphate or acetate buffers, tonicity agents such as salts or amino acids, and surfactant polyoxyethylene-sorbitanmonooleate (TWEEN 80). Further the pharmaceutical composition can be lyophilized.

In some embodiments, a pharmaceutical composition for treating bleeding disorders comprises at least one excipient, FII and FXa, wherein the molar ratio of FXa to FII is more than about 1:20,000, more than about 1:19,000, more than about 1:18,000, more than about 1:17,000, more than about 1:16,000, more than about 1:15,000, more than about 1:14,000, more than about 1:13,000, more than about 1:12,000, more than about 1:11,000, more than about 1:10,000, more than about 1:9,000, more than about 1:8,000, more than about 1:7,000, more than about 1:6,000, more than about 1:5,000, more than about 1:4,000, more than about 1:3,000, more than about 1:2,000, more than about 1:1,000, more than about 1:950, more than about 1:900, more than about 1:850, more than about 1:800, more than about 1:750, more than about 1:700, more than about 1:650, more than about 1:600, more than about 1:550, more than about 1:500, more than about 1:450, more than about 1:400, more than about 1:350, more than about 1:300, more than about 1:250, more than about 1:200, more than about 1:150, more than about 1:100, more than about 1:95, more than about 1:90, more than about 1:85, more than about 1:80, more than about 1:75, more than about 1:70, more than about 1:65, more than about 1:60, more than about 1:55, more than about 1:50, more than about 1:45, more than about 1:40, more than about 1:35, more than about 1:30, more than about 1:25, more than about 1:20, more than about 1:15, more than about 1:10, or more than about 1:5.

In other embodiments, a pharmaceutical composition for treating bleeding disorders comprises at least one excipient, FII and FXa, wherein the molar ratio of FXa to FII is about 1:19,999, about 1:19,500, about 1:18,500, about 1:17,500, about 1:16,500, about 1:15,500, about 1:14,500, about 1:13,500, about 1:12,500, about 1:11,500, about 1:10,500, about 1:9,500, about 1:8,500, about 1:7,500, about 1:6,500, about 1:5,500, about 1:4,500, about 1:3,500, about 1:2,500, about 1:1,500, about 1:950, about 1:900, about 1:850, about 1:800, about 1:750, about 1:700, about 1:650, about 1:600, about 1:550, about 1:500, about 1:450, about 1:400, about 1:350, about 1:300, about 1:250, about 1:200, about 1:150, about 1:100, about 1:95, about 1:90, about 1:85, about 1:80, about 1:75, about 1:70, about 1:65, about 1:60, about 1:55, about 1:50, about 1:45, about 1:40, about 1:35, about 1:30, about 1:25, about 1:20, about 1:15, about 1:10, or about 1:5.

In yet other embodiments, a pharmaceutical composition for treating bleeding disorders comprises at least one excipient and about 0.1 mg/kg of FII and about 800 ng/kg of FXa, about 0.15 mg/kg of FII and about 700 ng/kg of FXa, about 0.2 mg/kg of FII and about 600 ng/kg of FXa, about 0.25 mg/kg of FII and about 500 ng/kg of FXa, about 0.3 mg/kg of FII and about 400 ng/kg of FXa, about 0.35 mg/kg of FII and about 300 ng/kg of FXa, about 0.4 mg/kg of FII and about 200 ng/kg of FXa, about 0.45 mg/kg of FII and about 200 ng/kg of FXa, or about 0.5 mg/kg of FII and about 100 ng/kg of FXa. In other embodiments, a composition for treating bleeding disorders comprises about 0.44 mg/kg of FII and about 826 ng/kg of FXa. In other embodiments, a composition for treating bleeding disorders comprises about 4.4 mg/kg of FII and about 275 ng/kg of FXa.

In certain embodiments, a pharmaceutical composition for treating bleeding disorders comprises at least one excipient and about 0.1 mg/kg to about 0.5 mg/kg of FII and about 600 ng/kg to about 1100 ng/kg of FXa, about 0.5 mg/kg to about 1 mg/kg of FII and about 500 ng/kg to about 1000 ng/kg of FXa, about 1 mg/kg to about 1.5 mg/kg of FII and about 450 ng/kg to about 950 ng/kg of FXa, about 2.0 mg/kg to about 2.5 mg/kg of FII and about 400 ng/kg to about 900 ng/kg of FXa, about 2.5 mg/kg to about 3.0 mg/kg of FII and about 350 ng/kg to about 850 ng/kg of FXa, about 3.5 mg/kg to about 4.5 mg/kg of FII and about 300 ng/kg to about 600 ng/kg of FXa, or about 4.5 mg/kg to about 5.5 mg/kg of FII and about 200 ng/kg to about 600 ng/kg of FXa. In other embodiments, a composition for treating bleeding disorders comprises about 0.2 mg/kg to about 1 mg/kg of FII and about 560 ng/kg to about 1100 ng/kg of FXa. In other embodiments, a composition for treating bleeding disorders comprises about 1.2 mg/kg to about 5 mg/kg of FII and about 200 ng/kg to about 540 ng/kg of FXa.

To determine the molar ratio of FXa to FII useful in treating bleeding disorders, a translational in vitro-to-in vivo approach was used. First, combinations were tested in vitro for their procoagulant potential in comparison to FEIBA® using a global hemostatic assay system with human plasma. Second, selected FII/FXa plasma concentrations were translated into doses for hemophilia-induced rabbits and the efficacy assessed in an acute bleeding model.

The experiments for the in vitro and in vivo evaluation of different ratios of human FII and FXa were performed with carefully selected commercially available plasma-derived proteins from Enzyme Research Laboratories. For the selection, proteins from different suppliers had been tested for purity (Silver staining, Western Blotting), activity (thrombin generation in human and rabbit plasma), concentration and pricing.

Knowing the composition and active components of the multi-component FEIBA®, a combination of two coagulation factors was generated: human FII and FXa. A human plasma-based calibrated automated thrombography (CAT) assay was applied to identify FII/FXa combinations at specific ratios that had a similar in vitro procoagulant effect in FVIII-inhibited plasma as FEIBA®. Three FII/FXa ratios were selected, translated into preclinical doses and efficacy assessed in a rabbit bleeding model. Three compositions, the first with 100% FII and FXa (same as in FEIBA®), the second with 10% prothrombin and 300% FXa, and FEIBA® showed statistically significant efficacy. The latter dose contains ~20-fold less FII and 4-fold more FXa compared to previous studies. The dose with 25% FII and 200% FXa was not effective. The observed hemostatic effect appears to be mediated by neither FII nor FXa alone. In conclusion, the ratio of FII and FXa was adjusted so that activity and in vivo efficacy were unaltered and recombinant protein production for a recombinant version of FII/FXa remained feasible.

Example 1

In Vitro Evaluation of FXa/FII Combination in a Thrombin Generation Assay

The calibrated automated thrombography (CAT) assay has been used to monitor the pro- and anticoagulant effects of substances in human plasma. The thrombogram describes the concentration of thrombin in clotting plasma and the CAT is therefore a general physiologic function test of the hemostatic system. The assay is based on the measurement of fluorescence that is generated by the cleavage of the fluorogenic substrate Z-G-G-R-AMC by thrombin over time upon initiation of coagulation by Tissue Factor (TF). The assay is performed on a Thrombograph™, a 96-well plate fluorometer available from Thermo Scientific, and uses a thrombin calibrator that is needed to correct for inner filter effect, donor-to-donor variability in color of plasma, substrate depletion and instrumental differences.

The procoagulant activity of various combinations of plasma-derived FII (140-1400 nM) and FXa (0.035-0.21 nM) was assessed by CAT in FVIII-inhibited plasma. A normal human plasma pool (George King Biomedical) was treated with 50 Bethesda units (BU)/mL goat anti-FVIII plasma (Baxter). Corn trypsin inhibitor (CTI, 40 μg/mL, Haematologic Technologies) was added to inhibit pre-activation by factor XIIa. Clotting was triggered with 1 pM TF+4 μM phospholipids (PL) (PPP LOW reagent, Thrombinoscope BV). Thrombin generation was monitored at 37° C. for 90 min in a Fluoroskan Ascent reader (Thermo Scientific; wavelength 390/460 nm) after recalcification. Duplicate measurements were performed for each sample.

A CAT protocol optimized for rabbit plasma (40 μL/mL CTI, final plasma dilution of 1:3, 0.6 pM TF and 4 μM PL) was used to confirm in spike-in studies that human FII and FXa are also active in rabbit plasma. The same CAT protocol was used for the analysis of ex vivo rabbit plasma samples in the context of the nail clip bleeding study.

The feasibility of reducing the amount of FII within the FII/FXa combination was first tested in a human-plasma based CAT assay. Starting point was the FXa:FII ratio as found in FEIBA® (1:20,000), which is equivalent to plasma concentrations of 0.07 nM FXa and 1400 nM FII. The effect of decreasing the FII concentration from 1400 nM (100% FII) to 140 nM (10% FII) while keeping the FXa concentration constant at 0.14 nM (200%) is shown in FIG. 1. It was observed that 0.14 nM FXa alone corrected thrombin generation in FVIII-inhibited plasma as well as 1 U/mL FEIBA®. The presence of FII increased the endogenous thrombin potential (ETP) in a dose-dependent manner and resulted in higher thrombin generation than 1 U/mL FEIBA®.

Figure 2:
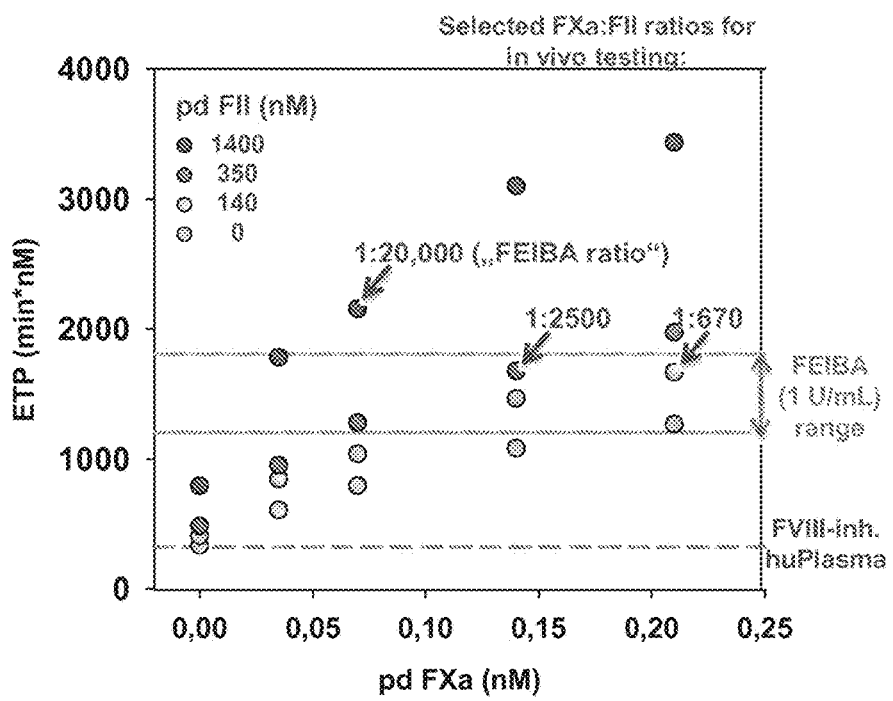
FIG. 2 is a diagram illustrating cross-titration of FII and FXa in a calibrated automated thrombography (CAT) assay with FVIII-inhibited human plasma.

Subsequently, a wider concentration range of FII (105 nM to 1400 nM) and FXa (0.035 to 0.21 nM) was cross-titrated in the CAT assay (FIG. 2). A target range for the desired procoagulant activity of FII/FXa was established by testing the effect of 20 different FEIBA® lots at 1 U/mL. The ETP was used as comparative CAT parameter as it showed the most significant change in response to FII/FXa. A few FII/FXa combinations were identified to lie within the range of FEIBA® activity in correcting thrombin generation in FVIII-inhibited plasma, resulting in 100% to 7.5% prothrombin and 100 to 300% FXa as in FEIBA® (Table 1). A slight decrease in thrombin generation upon FII reduction can be compensated by a moderate increase in FXa. Three combinations were selected to be tested in an in vivo efficacy model in hemophilia A-induced rabbits.

TABLE 1

Summary of FXa:FII molar ratios that reached a procoagulatant effect (based on ETP values) equivalent to 1 U/mL FEIBA ® in a CAT assay with FVIII-inhibited human blood.

| FII (nM) | FXa (nM) | FII (% of amount in FEIBA) | FXa (% of amount in FEIBA) | Ratio |
|---|---|---|---|---|
| 1400* | 0.07* | 100 | 100 | 1:20,000* |
| 700 | 0.07 | 50 | 100 | 1:10,000 |
| 350 | 0.07 | 50 | 100 | 1:5000 |
| 350 | 0.14 | 25 | 200 | 1:2500 |
| 140 | 0.14 | 10 | 200 | 1:1000 |
| 140 | 0.21 | 10 | 300 | 1:670 |
| 105 | 0.21 | 7.5 | 300 | 1:500 |

(*indicates the ratio as it is found in FEIBA ®. Combinations having FXa:FII molar ratios of 1:20,000, 1:2,500, and 1:670 were selected for in vivo study.)

Example 2

In Vivo: Proof of Concept Efficacy in Hemophilia-Induced Rabbit Model

Figure 3A:
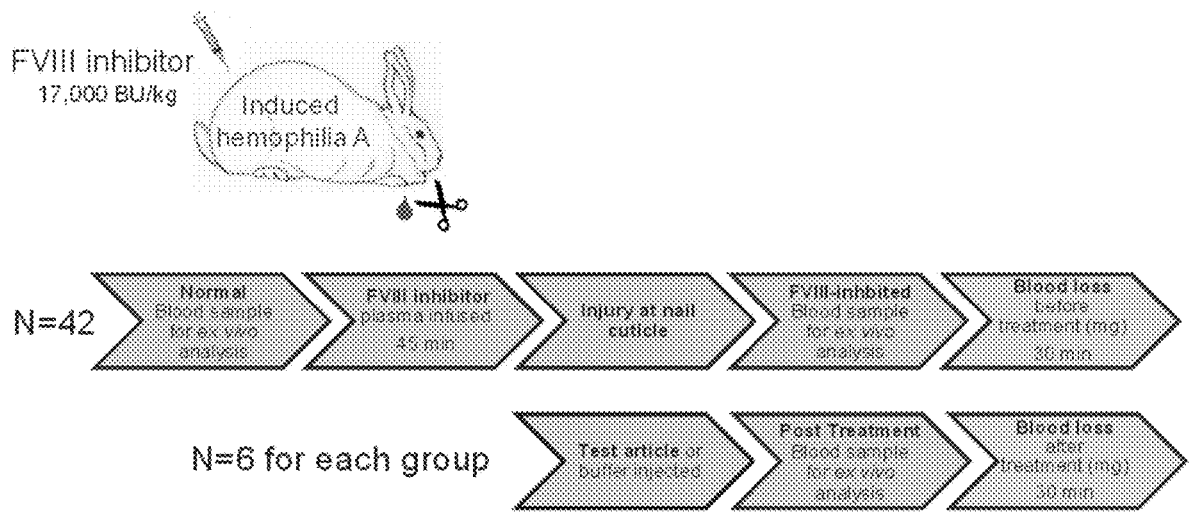
FIGS. 3A and 3B illustrate the acute efficacy of different combinations of FII and FXa in a nail-clip bleeding model in hemophilia-induced rabbits.

The aim of this proof-of-concept study was to assess the efficacy of three FII/FXa doses administered together or alone in a nail-clip bleeding model in FVIII-inhibited rabbits (FIG. 3A). The dose with highest FII amount was 4.4 mg/kg FII+275 ng/kg FXa and is defined as "FEIBA® ratio" and 100% for both FII and FXa. The second dose 1.1 mg/kg FII+551 ng/kg FXa had FII reduced to 25% and FXa increased to 200%. The third dose 0.44 mg/kg FII+826 ng/kg FXa had FII reduced to 10% and FXa increased to 300%. Efficacy was determined for each treatment in terms of reduced blood loss after treatment in comparison to a buffer-only control group. FEIBA® (75 U/kg) served as a positive control.

Conscious New Zealand white (NZW) rabbits were intravenously administered with 2 mL/kg FVIII inhibitor (17,000 BU/kg) to deplete endogenous FVIII. After approximately 20 mins, the animals were anesthetized by subcutaneous injection with 5 mg/kg xylazine and 75 mg/kg ketamine. Rabbits were laid on a heating pad to prevent hypothermia, and the hair on digit II of the right hind limb shaved. The nail was cut 3 mm from the distal edge of the blood supply matrix 45 min after application of inhibitor plasma. Blood was then collected for 30 min in a tube with saline (room temperature) by immersing the bleeding nail. After this first observation period, the saline tubes were exchanged to prevent drying of the inflicted wound. Six male NZW rabbits were used per group. The animals received intravenous treatment with test or control item. Ten min after application of test or control item, the bleeding nail was inserted in a third tube with saline, and blood collected again for 30 min. For each tube, the amount of blood was measured gravimetrically. The experimental procedure is depicted in FIG. 3A. The rabbits were killed at the end of the second observation period by injecting an overdose of pentobarbital.

Figure 3B:
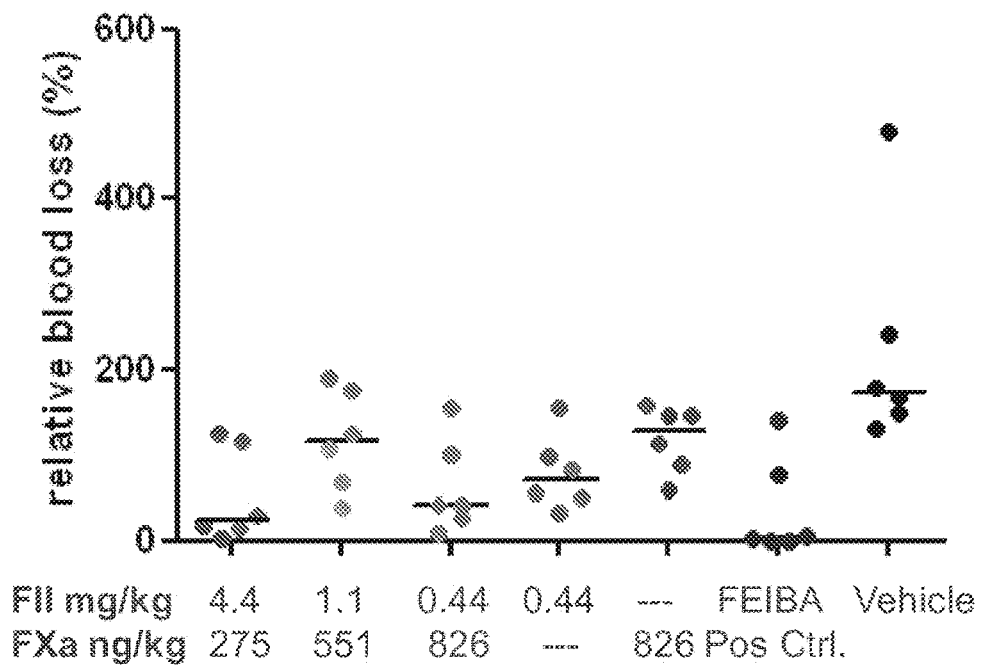

Blood loss within 30 min before and after application of treatment was summarized by treatment group using medians, inter-quartile ranges (IQRs), ranges (minimum to maximum), arithmetic means and coefficients of variation as depicted in FIG. 3B. The efficacious dose of about 826 ng/kg of FXa and about 0.44 mg/kg of FII has a 90% reduced FII amount compared to the FEIBA® ratio. The results demonstrate that lowering the FII amount and slightly increasing FXa is sufficient to correct bleeding in a hemophilia animal model.

Animals were pretreated with FVIII inhibitor to achieve transient hemophilia A, closely mimicking the situation in hemophilic patients with inhibitors. The efficacy of test and control item was assessed using a nail-clip bleeding model; thrombelastography and CAT assay were performed to gain additional information (see Example 3). In the nail-clip bleeding assay, there was a statistically significantly lower blood loss with FEIBA® (75 U/kg) than with buffer (p=0.02273) providing statistical evidence that the complex experimental system was operating correctly. From an exploratory point of view, treatment with FII (4.38 mg/kg)+ FXa (275 ng/kg) and FII (0.44 mg/kg)+FXa (826 ng/kg) showed a statistically significantly smaller blood loss than buffer (p≤0.01403). In conclusion, it is feasible to reduce the amount of FII in the FII/FXa combination drastically by slightly increasing the amount of FXa without losing the hemostatic efficacy. This would make the commercial production of recombinant FII for a recombinant combination of FII/FXa economically easier.

Example 3

Ex Vivo Analysis of Rabbit Whole Blood or Plasma by Thromboelastography and CAT Assay Blood samples of FVIII-inhibited rabbits after administration of FEIBA®, FII or FXa alone or in combination, or buffer were analyzed ex vivo by thromboelastography (TEG). Measurements were performed using a TEG hemostasis analyzer 5000 (Haemonetics Corp, USA) at 37° C. Blood was sampled before and 45 min after administration of FVIII-inhibitor plasma, immediately after administration of test or control item, and at the end of the second bleeding observation period (approximately 40 min after test item administration). Blood was sampled by puncturing a central ear artery using a 2-mL syringe (20 gauge needle) filled with 0.1 mL sodium citrate and 21 µL CTI (Haematologic Technologies, 3 mg/mL). The animals were exsanguinated by cardiac puncture at the end of the second bleeding observation period. 1 mL of citrated whole blood (blood:citrate=10:1) was drawn. Each blood sample (320 µL) was mixed with 20 µL of TF. (0.04 pM final concentration) and re-calcified with 20 µL of a 0.2 M $CaCl_2$ solution in a pre-warmed TEG cuvette at 37° C. Measurement was started immediately and duplicates measured in parallel for each blood sample. The TEG run was either stopped after all relevant measurements were obtained or cancelled after 2 h if no clot formed. The TEG parameters of clotting time (R-time), speed of clot formation (K-time) rapidity of clot strengthening (angle) and maximum clot firmness (MA) were recorded.

Figure 4:
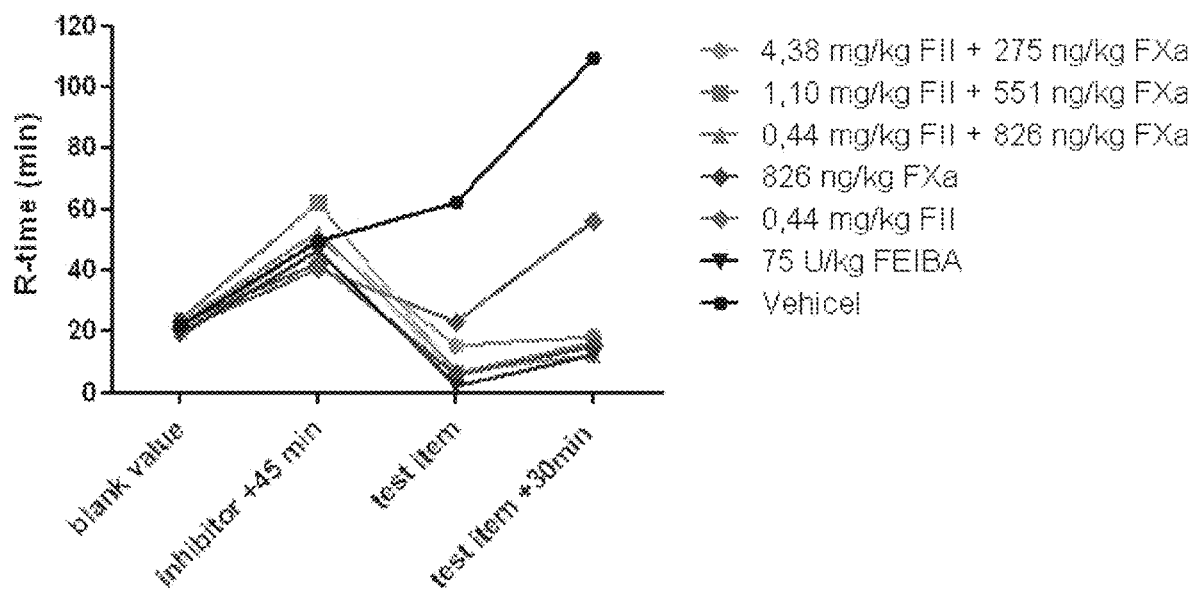
FIG. 4 is a diagram illustrating the ex vivo analysis of whole blood samples from FVIII-inhibited rabbits treated with FII and FXa alone or in combination.

Ex vivo analysis of whole rabbit blood by TEG (FIG. 4) 5 min after treatment with 75 U/kg FEIBA® showed a statistically significant reduction in R-time compared with buffer ($p<0.001$). The same was true for all other treatment groups ($p<0.001$). The effect was still observed at the end of the study, approximately 40 min after test article administration, except for the FII alone group where the clotting time was back at the level of FVIII-inhibited blood. In general, the TEG assay appeared to be very sensitive to FXa. While FXa alone was not efficacious for the reduction of relative blood loss in vivo, the blood samples showed significantly reduced R-times ex vivo.

Figure 5:
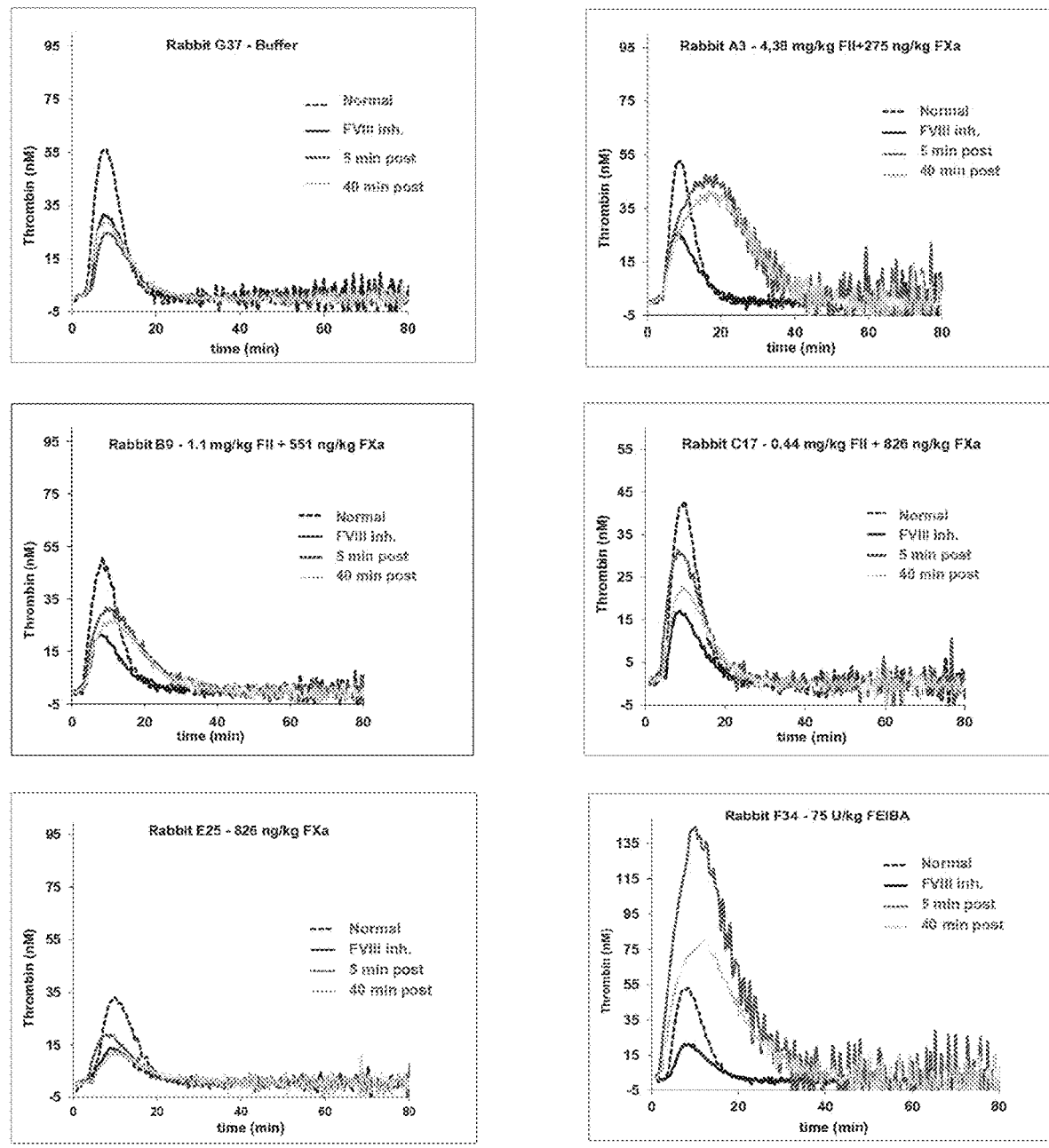
FIG. 5 is a diagram illustrating the CAT analysis of plasma samples from FVIII-inhibited rabbits treated with FII and FXa alone or in combination.

Rabbit plasma samples were also analyzed by CAT analysis. FIG. 5 shows representative thrombin generation profiles for one animal of each dosing group at all four timepoints. The group dosed with FII alone is not represented, but had no effect on thrombin generation. Administration of the positive control (75 U/mL FEIBA®) led to the largest increase in thrombin generation 5 min after treatment. Combined treatment of FVIII-inhibited rabbits with plasma-derived human FII and FXa showed a beneficial effect on thrombin generation in rabbit plasma and reached ETP values that were closer to the normal baseline than the FEIBA® control. A moderate increase in thrombin generation is preferable over massive thrombin generation as this may be an indicator for thrombogenic activity. The most obvious difference between the different FII/FXa doses in the CAT assay is the high ETP values (area under the curve) of the thrombin profiles depending on the FII concentration. This can be explained by the additional substrate in the form of prothrombin that is introduced to the plasma sample, which is quickly activated to thrombin by FXa. Plasmas of animals dosed with FII or FXa administered alone and the buffer did not affect thrombin generation significantly.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A method of treating a bleeding disorder comprising administering a composition including prothrombin (FII) and activated factor X (FXa) wherein the molar ratio of FXa to FII ranges between 1:10,000 and 1:500, and wherein the concentration of FII in the composition is about 105-700 nM and the concentration of FXa in the composition is about 0.07-0.21 nM.

2. The method of claim 1, wherein the FII and FXa is plasma derived or recombinant.

3. The method of claim 1, wherein the concentration of FII is about 0.44 mg/kg and the concentration of FXa is about 826 ng/kg.

4. The method of claim 1, wherein the concentration of FII is about 0.2 mg/kg to about 1 mg/kg and the concentration of FXa is about 560 ng/kg to about 1100 ng/kg.

5. The method of claim 1, wherein the concentration of FII is about 1.2 mg/kg to about 5 mg/kg and the concentration of FXa is about 200 ng/kg to about 540 ng/kg.

6. The method of claim 1, wherein the bleeding disorder is hemophilia A, hemophilia B, von Willebrand disease, congenital hemophilia A with inhibitors or acquired hemophilia A with inhibitory auto antibodies to FVIII, congenital hemophilia B with inhibitors or acquired hemophilia B with inhibitory auto antibodies to FIX, blood loss from trauma, FVII deficiency, FV deficiency, FX deficiency, FXI deficiency, FXIII deficiency, fibrinogen deficiency, prothrombin deficiency, dilutional coagulopathy, thrombocytopenia, blood loss from high-risk surgeries, intracerebral hemorrhage, von Willebrand disease with inhibitors to von Willebrand factor, or combinations thereof.

7. The method of claim 1, wherein the composition is administered via parenteral injection, subcutaneous injection, intramuscular injection, or intravenous injection.

8. The method of claim 1, wherein the composition is a pharmaceutical composition.

9. The method of claim 8, wherein the pharmaceutical composition further comprises at least one excipient.

10. The method of claim 9, wherein the excipient is selected from a group consisting of water, NaCl or other salts for isotonicity, 5% dextrose in water, buffered solutions with a pH of 2-8, trehalose, mannitol, sorbitol, phosphate buffers, acetate buffers, tonicity agents such as salts or amino acids, and surfactant polyoxyethylene-sorbitanmonooleate.

11. The composition of claim 1, wherein the molar ratio of FXa to FII ranges between 1:2,500 and 1:500.

12. The composition of claim 1, wherein the composition is lyophilized.

* * * * *